United States Patent
Egli et al.

(10) Patent No.: US 12,296,330 B2
(45) Date of Patent: May 13, 2025

(54) PIPETTING UNIT AND PIPETTING METHOD FOR CLOSED LIQUID CONTAINERS

(71) Applicant: Roche Diagnostics Operations, Inc., Indianapolis, IN (US)

(72) Inventors: Ronald Egli, Aarau (CH); Mirko Klingauf, Schlieren (CH); Daniel Ott, Baar (CH); Jerome Wiss, Meierskappel (CH)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 1000 days.

(21) Appl. No.: 17/099,884

(22) Filed: Nov. 17, 2020

(65) Prior Publication Data
US 2021/0170390 A1    Jun. 10, 2021

(30) Foreign Application Priority Data

Dec. 6, 2019 (EP) .................................... 19214244

(51) Int. Cl.
| | |
|---|---|
| *B01L 3/02* | (2006.01) |
| *G01N 7/00* | (2006.01) |
| *G01N 33/50* | (2006.01) |
| *G01N 35/10* | (2006.01) |

(52) U.S. Cl.
CPC .............. *B01L 3/021* (2013.01); *G01N 7/00* (2013.01); *G01N 33/5091* (2013.01); *B01L 2300/14* (2013.01); *B01L 2400/0475* (2013.01)

(58) Field of Classification Search
None
See application file for complete search history.

(56) References Cited

U.S. PATENT DOCUMENTS

| | | |
|---|---|---|
| 5,380,486 A | 1/1995 | Anami |
| 5,853,665 A | 12/1998 | Ade et al. |
| 5,918,291 A | 6/1999 | Inacu et al. |
| 5,935,523 A | 8/1999 | McCandless et al. |
| 6,805,842 B1 | 10/2004 | Bodner et al. |
| 2006/0127281 A1 | 6/2006 | Bjornson et al. |
| 2006/0228807 A1 | 10/2006 | Nagai et al. |

(Continued)

FOREIGN PATENT DOCUMENTS

| | | |
|---|---|---|
| CN | 101603968 | 12/2009 |
| CN | 201497691 | 6/2010 |

(Continued)

OTHER PUBLICATIONS

European Search Report issued Apr. 29, 2020 in Application No. EP 19214244.6, 2 pp.

*Primary Examiner* — Elizabeth A Robinson
*Assistant Examiner* — Brittany I Fisher
(74) *Attorney, Agent, or Firm* — Woodard, Emhardt, Henry, Reeves & Wagner, LLP

(57) ABSTRACT

An in-vitro diagnostic device including a pipetting unit and a pipetting method, which allow for a more reproducible and more precise pipetting of liquids, when piercing through a lid of a closed liquid container is required. The pipetting unit is controlled to repeat penetration of the lid of the closed liquid container if the pressure difference between the interior of the liquid container and the surrounding is outside an allowable predefined pressure range.

14 Claims, 4 Drawing Sheets

(56) References Cited

U.S. PATENT DOCUMENTS

| | | | |
|---|---|---|---|
| 2006/0263250 A1* | 11/2006 | Blouin | G01N 35/1079 422/63 |
| 2009/0100942 A1 | 4/2009 | Maeda et al. | |
| 2014/0106467 A1* | 4/2014 | Hutter | G01N 35/1016 436/180 |
| 2014/0302610 A1 | 10/2014 | Blouin et al. | |
| 2019/0270086 A1 | 9/2019 | Harding et al. | |

FOREIGN PATENT DOCUMENTS

| | | |
|---|---|---|
| EP | 1614468 B1 | 12/2006 |
| JP | H05-264561 A | 10/1993 |
| WO | 2009/024710 A1 | 2/2009 |

\* cited by examiner

PIPETTING UNIT AND PIPETTING METHOD FOR CLOSED LIQUID CONTAINERS

CROSS-REFERENCE TO RELATED APPLICATIONS

This application claims priority to European Patent Application No. 19214244.6, filed 6 Dec. 2019, the disclosure of which is hereby incorporated by reference in its entirety.

FIELD OF THE DISCLOSURE

The present disclosure relates to an in-vitro diagnostic device comprising a pipetting unit and to a method for pipetting a liquid through a lid of a liquid container.

BACKGROUND

Reliable and precise pipetting of liquid volumes is a requirement in many in-vitro diagnostic devices. In particular, it is important to achieve a precise ratio of sample volume versus reagent volume. This is a prerequisite for achieving measurement results that are correctly interpretable in a medical context and that allow health care professionals to derive accurate diagnoses.

Various pipetting procedures have been established in different in-vitro diagnostic devices in the past. However, the pipetting procedure of aspirating a volume of liquid through a lid of a closed liquid container remains a specifically challenging one. Typically, a probe of a pipetting unit is used to pierce through the lid of a liquid container and then aspirate liquid therefrom. In such a procedure, it is difficult to achieve pipetting precision and reproducibility, especially for small liquid volumes to be aspirated, e.g., of few microliters, due to various reasons. On the one hand, piercing of a lid can lead to blockage or physical damages of the probe, depending on the material properties of the lid (typically elastomeric materials). On the other hand, piercing and aspirating liquid from a closed liquid container provides a further challenge: it often occurs that a negative pressure, i.e., a pressure lower than atmospheric pressure, e.g., occurring when an evacuated container is insufficiently filled by a sample, or overpressure, i.e., a pressure higher than atmospheric pressure, e.g., occurring when a liquid container is recapped, is created in the closed liquid container during pre-analytical manipulations. A pipetting unit may be constructed in a way that the probe is connected to a pump via a conduit containing system fluid and air gap(s) to prevent the aspirated liquid from the liquid container from mixing with the system fluid. In such a case, negative pressure in the liquid container may lead to an expansion of the air gap(s) in the conduit, leading to incorrect aspiration volumes. Similarly, an overpressure in the liquid container can lead to a compression of such an air gap, thus leading to incorrect aspiration volumes, or even to a mixing of liquid from the liquid container and system fluid, thereby unintentionally diluting the liquid. Further, when aspirating a defined volume of liquid from a liquid container having a negative pressure or overpressure, it may occur that the position of the aspirated liquid volume within the conduit is shifted when withdrawing the probe through the lid of the container due to a pressure compensation effect. Altogether, these effects may lead to aspirating of incorrect volumes of liquid into the probe as well as dispensing of incorrect volumes of liquid out of the probe.

One known approach to overcome this problem is to unload the affected liquid containers from the in-vitro diagnostic device and remove the lids manually. The liquid containers are then re-inserted into the in-vitro diagnostic device. However, this approach does not only increase the manual interaction steps with the in-vitro diagnostic device, but thereby also decreases throughput, delays the result output, and shortens the walk-away time, ultimately leading to higher overall laboratory costs, besides increasing the risk of contamination and/or getting exposed to potentially infectious biological material.

It is therefore important to overcome the above mentioned problems by providing a way to increase pipetting precision and reliability when handling closed liquid containers, especially when pressure differences between the interior of a liquid container and the surrounding atmospheric pressure are outside of an acceptable range.

SUMMARY

It is against the above background that the embodiments of the present disclosure provide certain unobvious advantages and advancements over the prior art. In particular, the inventors have recognized a need for improvements in a pipetting unit and pipetting method for closed liquid containers.

Although the embodiments of the present disclosure are not limited to specific advantages or functionality, it is noted that the present disclosure provides an in-vitro diagnostic device comprising a pipetting unit and a pipetting method, which provide for a more reproducible and more precise pipetting of liquids, when piercing through a lid of a closed liquid container is required. This is achieved by an automated and feedback-controlled piercing process that can compensate for pressure differences between the interior of the liquid container and the surrounding and thereby reduce the risk of pipetting errors. In case the pressure difference and thus increased pipetting precision cannot be achieved, the method ensures that pipetting is prevented. The automated piercing process is distributed across different cycle times to optimize throughput.

In accordance with one embodiment of the present disclosure, an in-vitro diagnostic device comprising a pipetting unit for pipetting a liquid through a lid of a liquid container and comprising a pressure sensor for detecting a pressure in the liquid container is provided. The in-vitro diagnostic device further comprises a controller configured to control the pipetting unit to penetrate the lid of the liquid container. If the pressure sensor detects a pressure outside of a predefined pressure range in the liquid container, the controller controls the pipetting unit to repeat penetration. Only upon detecting a pressure within the predefined pressure range, the controller controls the pipetting unit to aspirate an aliquot of the liquid for carrying out an in-vitro diagnostic test.

In accordance with another embodiment of the present disclosure, a computer implemented method for pipetting a liquid through a lid of a liquid container is provided, the method comprising penetrating by a pipetting unit the lid of the liquid container, measuring by a pressure sensor the pressure in the liquid container and upon detecting a pressure outside of a predefined pressure range in the liquid container, repeating penetration, and only upon detecting a pressure within the predefined pressure range aspirating an aliquot of the liquid for carrying out an in-vitro diagnostic test.

These and other features and advantages of the embodiments of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Figure 1:
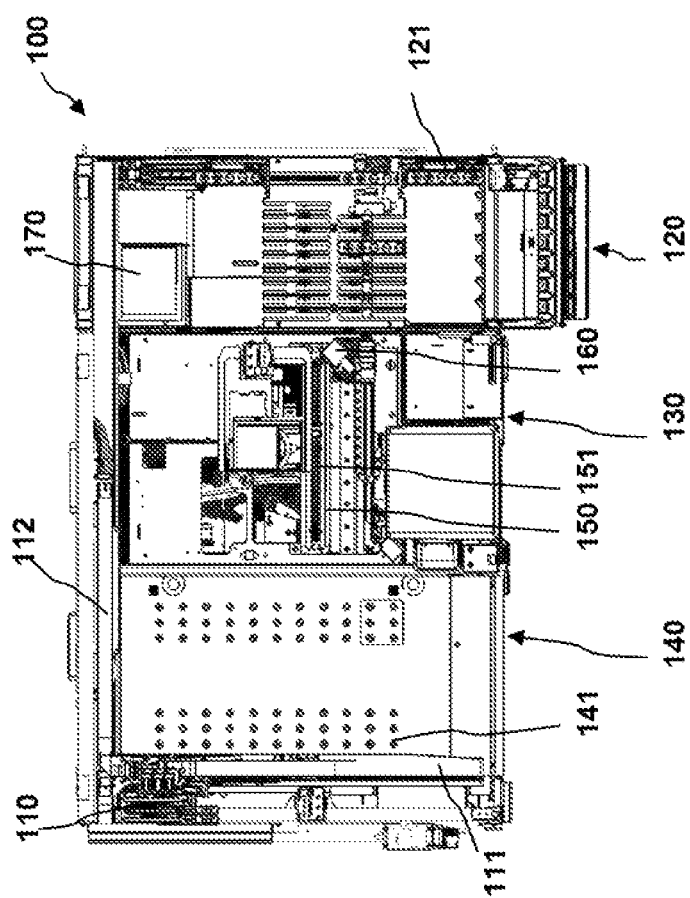
FIG. 1 is a partial top view of an in-vitro diagnostic device.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

An "in-vitro diagnostic device" as used herein refers to an automated analytical apparatus dedicated to obtaining an analytical measurement value, or to an automated pre-analytical or post-analytical apparatus or combinations thereof. An in-vitro diagnostic device can follow a particular operating workflow, e.g., execute a number of processing steps, which are optimized for certain types of analyses, e.g., clinical chemistry, immunochemistry, coagulation analysis, hematology analysis, mass spectrometry analysis, etc. The expression "processing steps" thereby refers to physically executed processing steps such as loading/unloading, centrifuging, pipetting, incubating, mixing, transporting, heating, cooling, measuring, detecting and the like. The in-vitro diagnostic device may comprise one or many "functional units" that are dedicated to executing these processing steps, e.g., a conveyor, a gripper, a centrifuge, a pipetting unit, an incubation unit, an analytical measurement unit, etc. The in-vitro diagnostic device may have different configurations according to the need and/or according to the desired laboratory workflow. It can be operated as stand-alone device or in conjunction with one or more other in-vitro diagnostic devices and/or modules. A "module" is a work cell, which has a dedicated function. This function can be analytical but can also be pre-analytical or post-analytical, or it can be an auxiliary function to any of the pre-analytical function, analytical function or post-analytical function. In particular, a module can be configured to cooperate with one or more other modules for carrying out dedicated tasks of a sample processing workflow, e.g., by performing one or more pre-analytical and/or analytical and/or post-analytical processing steps. Thus, the in-vitro diagnostic device may comprise one analytical apparatus or a combination of any of such analytical apparatuses with respective workflows, where pre-analytical and/or post analytical modules may be coupled to individual analytical apparatuses or be shared by a plurality of analytical apparatuses. Alternatively, pre-analytical and/or post-analytical functions may be performed by units integrated in in-vitro diagnostic devices. Examples of analytical apparatuses are clinical chemistry analyzers, immunochemistry analyzers, coagulation analyzers, hematology analyzers, urine analyzers, mass spectrometry analyzers and nucleic acid analyzers that are used for the qualitative and/or quantitative detection of analytes present in the liquids, to detect the result of chemical or biological reactions and/or to monitor the progress of chemical or biological reactions. Examples of pre-analytical processing steps performed by a pre-analytical apparatus are loading and/or unloading of liquid containers and/or consumables, transporting of liquid containers and/or consumables, identification of liquid containers and/or consumables, washing of liquid containers and/or probes and/or pipette tips, liquid quality checks, fill level checks, liquid container sorting, centrifuging, heating, cooling, pipetting, aliquoting, mixing of different liquids (e.g., samples, reagents, solvents, diluents, buffers), e.g., to enable further processing by an analytical apparatus, decapping, recapping, and the like. Post-analytical processing steps performed by a post-analytical apparatus can be at least in part similar to the pre-analytical processing steps performed by a pre-analytical apparatus, and may especially include sorting, reformatting, archiving or storing and/or retrieving of liquid containers or consumables and the like.

The term "liquid" is herein used to indicate any type of liquid material required to perform a diagnostic test, i.e., an in-vitro diagnostic analysis. Examples are a sample, a reagent, a dilution liquid, a mixture or solution of one or more samples and/or one or more reagents and/or one or more dilution liquids. The term "sample", as used herein, refers to a liquid material suitable for being pipetted and being subjected to an in-vitro diagnostic analysis, e.g., in order to detect one or more analytes of interest suspected to be present therein or to measure a physical parameter of the sample as such, e.g., pH, color, turbidity, viscosity, coagulation time, etc. The sample can be derived from any biological source, such as a physiological fluid, including, blood, saliva, sputum, ocular lens fluid, cerebrospinal fluid (CSF), sweat, urine, milk, ascites fluid, mucous, synovial fluid, peritoneal fluid, pleural fluid, amniotic fluid, tissue, bone marrow, feces, cells or the like. The sample can be pretreated prior to use, such as preparing plasma from blood, diluting viscous fluids, lysis or the like; methods of treatment can involve filtration, centrifugation, distillation, concentration, separation, purification, liquid or solid-phase extraction, matrix removal, inactivation of interfering components, and the addition of reagents. A sample may be used directly as obtained from the source or following a pretreatment to modify the character of the sample, e.g., after being diluted with another solution or after having being mixed with reagents, e.g., to carry out one or more in-vitro diagnostic tests. The term "sample" as used herein is therefore not necessarily used to indicate the original sample but may also relate to a sample which has already been processed (pipetted, diluted, mixed with reagents, enriched, purified, amplified, etc.). The term "sample" may further refer to liquids that contain known levels of analytes and are used to confirm the diagnostic device operability, e.g., quality controls and/or calibrators. The term "reagent" is generally used to indicate a liquid or substance required for treatment of a sample. Reagents may be any liquid, e.g., a solvent or chemical solution, which can be mixed with a sample and/or other reagent in order, e.g., for a reaction to occur, or to enable detection. A reagent may be for example a diluting liquid, including water, it may comprise an organic solvent, it may comprise a detergent, and/or it may be a buffer. A reagent in the more strict sense of the term may be a liquid solution containing a reactant, typically a compound or agent capable, e.g., of binding to or chemically transforming one or more analytes present in a sample. Examples of reactants are enzymes, enzyme substrates, conjugated dyes, protein-binding molecules, nucleic acid binding molecules, antibodies, chelating agents, promoters, inhibitors, epitopes, antigens, and the like.

The term "aliquot of the liquid" as used herein refers to a partial volume of a liquid that is aspirated by the pipetting unit and designated for carrying out a diagnostic test. The aliquot may thereby be subjected to the diagnostic analysis itself, e.g., if the liquid is a sample, or it may be required to enable a biochemical or chemical or physical reaction, e.g., by combining an aliquot of sample with one or more aliquots of one or more reagents. Aliquots of the liquid may, e.g., be dispensed in a reaction vessel and/or detection vessel, e.g., a cuvette, if for example the diagnostic analysis is based on optical measurement, or any other receiving container depending on the particular workflow and the particular detection and analytical methods.

The term "liquid container" is herein used to indicate a container comprising a body and an inner space adapted to receive liquids. Samples are typically provided in sample tubes and therefore are typically aspirated therefrom. The term "liquid container" may therefore refer to a sample tube. A "sample tube" is either a sample collection test tube also called "primary tube", which is used to receive a sample from a patient and to transport the sample contained therein to an analytical laboratory for an in-vitro diagnostic test, or a "secondary tube", which may be used to receive at least part of a sample from a primary tube. Sample tubes such as the primary tubes may be closed by a "lid", e.g., to prevent sample evaporation, contamination from the environment, and spillage of sample. The lid may comprise partially or be made entirely of a pierceable elastomeric material, e.g., a rubber stopper. Reagents are typically provided in different types of liquid containers, made e.g., of plastic material or glass, and may be embodied as individual containers, e.g., bottles, vials, punches, or packages or cassettes comprising one or more containers or compartments, comprising one or more different types of reagents, e.g., kits of reagents required for particular in-vitro diagnostic tests. Reagent containers are typically closed by a lid, e.g., to prevent evaporation and minimize the risk of contamination from the environment. The lid may be adapted to be opened and reclosed, e.g., every time that a volume of reagent needs to be aspirated. The lid may alternatively be adapted to be pierced so that aspiration may occur through the lid. The term "liquid container" may also refer to reaction vessels, e.g., to enable a reaction between one or more samples with one or more reagents and/or to enable analysis of a liquid contained therein. A reaction vessel may also be sealed by a lid (e.g., rubber stopper, foil, etc.) to prevent liquid evaporation or contamination from the environment, e.g., while being placed in an incubation station or while being placed in an analytical measurement unit of the in-vitro diagnostic device. The term "consumables" as used herein refers to any other auxiliary materials apart from samples and reagents that are required to perform diagnostic tests on an in-vitro diagnostic device. Examples of consumables are system fluids, bulk fluids, reaction vessels and vessel racks, measurement cuvettes, pipette tips, tip racks, microplates/microwell plates, wash buffer, etc.

In particular, the disclosed in-vitro diagnostic device comprises at least one pipetting unit. A "pipetting unit" is a functional unit of the in-vitro diagnostic device for pipetting liquids comprising for this purpose at least one aspiration probe that may function also as a dispensing probe. The term "pipetting" is herein used to indicate aspirating, i.e., withdrawing, a volume of liquid in a first step and dispensing a volume of liquid in a second step, wherein the volume of dispensed liquid may be different from the volume of aspirated liquid and wherein intermediate aspirating and/or dispensing steps may occur between the first step and the second step. The probe may be embodied as a reusable washable needle, e.g., a hollow steel needle, or as a pipette tip attached to a nozzle, e.g., a disposable pipette tip that is adapted to be regularly replaced, for example before pipetting a different type of liquid. According to the present disclosure, the probe is constructed in a manner that allows it to penetrate a lid closing a liquid container in order to aspirate liquid therefrom and without having to remove the lid. Removing the lid would not only require additional processing steps and thus reduce the in-vitro diagnostic device's throughput, but also carries the risk of contaminating instrument parts surrounding the liquid container through spilling and/or splashing, cross-contaminating other liquid containers located in close proximity, or reduce the on-board stability of a liquid in a liquid container (time that a liquid can be used before expiration). The probe may therefore be constructed from a solid and stable material, e.g., metal, steel, metal alloys, or hardened polymeric or composite material, and may be designed with a tapered end to allow penetration of the lid of a liquid container. As mentioned above, a lid of a liquid container may comprise or be entirely made of a pierceable elastomeric material. The elastomeric material is intended to allow penetration by, e.g., a pipetting probe, without losing its sealing properties, e.g., in order to prevent liquid evaporation, contamination from the environment, and spillage of liquid. In a one-time penetration, the elastomeric material almost completely reverts to its initial shape once the penetrating object is removed. However, it has been observed that multiple penetrations lead to multiple punctures and/or enlarged punctures and/or may turn the elastomeric material brittle, which ultimately results in gas exchange between the interior of the liquid container with the surrounding. This effect may be used in a liquid container having internal overpressure or negative pressure to reduce pressure differences or achieve pressure equilibration with ambient conditions. Typically, the pipetting unit is constructed in a way that the probe is connected to a pump via a conduit, i.e., a fluid/gas channel. The pump enables aspirating and dispensing liquids and/or gases, and may be of the type of a peristaltic pump, a syringe pump or the like. A fluid/gas channel may contain system fluid and possibly air gap(s) to prevent the aspirated liquid from a liquid container from mixing with the system fluid. Valves may be installed in the conduit to switch between different fluid/gas channels, depending on the planned or ongoing operation. E.g., in a washing operation, the valve is switched so that a connection between probe and a wash solution is established, which then allows for rinsing the pipetting unit with said wash solution. According to an embodiment, the pipetting unit may be moved by a head translation mechanism in one or two directions of travel in a plane, such as with guiding rails, and possibly in a third direction of travel orthogonal to the plane of translation, for example with a spindle drive. In another embodiment, the pipetting unit may be moved by a head rotational mechanism along a fixed circular path or part of circular path, and possibly in a third direction of travel orthogonal to the plane of rotation. According to yet another embodiment, the pipetting unit may be in a fixed position, whereas the in-vitro diagnostic device may be configured to move a liquid container with respect to the fixed pipetting unit. Combinations of the above movement options are also possible.

The pipetting unit further comprises a "pressure sensor". Various types of pressure sensing techniques are known in the art. The pressure sensor may be a resistive, a capacitive, a piezoelectric, an optical sensor, a sensor based on the MEMS technology (micro electro-mechanical system), or the like. Typically, piezoelectric pressure sensors are used in fluidic systems, such as, e.g., a pipetting unit comprising a probe connected to a pump via a conduit containing system fluid. In an embodiment, the pressure sensor may measure a "reference pressure", which may be the actual pressure outside of a closed liquid container (e.g., actual atmospheric pressure). In another embodiment, the reference pressure is a predefined value. Once the pipetting unit pierces the lid of the liquid container and the probe reaches the inside of the liquid container, an "internal pressure" is measured. The probe may be positioned, e.g., above or at the surface of the liquid. The surface of a liquid in a liquid container may be detected by a liquid level detector, which however is well known in the state of the art and will not further be explained in this disclosure. The controller monitors the deviation of the internal pressure from the reference pressure, where the internal pressure may only deviate by a predetermined value from the reference pressure in order to ensure pipetting precision. The thresholds that limit the allowable range can be determined by the manufacturer of the in-vitro diagnostic device or by a field service representative or in some cases by the operator of the in-vitro diagnostic device and are herein referred to as the "predefined pressure range". The predefined pressure range may be defined as absolute range, e.g., −350 mbar to +70 mbar, or as relative range, e.g., −35% to +10% with respect to the reference pressure. The predefined pressure range may further be defined based on the designated pipetting volume and/or the pipetting precision. For example, the smaller the liquid volumes are that need to be pipetted and/or the more precise the pipetting operations need to be, the narrower the predefined pressure range may be set, e.g., −25% to +5% with respect to the reference pressure. The term "outside of the predefined pressure range" refers to the internal pressure measurement either exceeding the upper threshold or falling below the lower threshold of the predefined pressure range. Should the internal pressure be outside of the predefined pressure range, the pipetting unit is prevented from aspirating an aliquot of the liquid for carrying out an in-vitro diagnostic test. The term "inside of the predefined pressure range" on the other hand refers to the internal pressure measurement falling within the upper and lower thresholds of the predefined pressure range. In this event, the pipetting unit is controlled to aspirate an aliquot of the liquid for carrying out an in-vitro diagnostic test.

A "controller" as herein used is a programmable logic controller or processor running a computer-readable program provided with instructions to perform operations in accordance with an operation plan. The term can mean central processing units, microprocessors, microcontrollers, reduced instruction circuits (RISC), application specific integrated circuits (ASIC), logic circuits, and any other circuit or processor capable of executing the functions/methods described herein. Regardless of the type of processor, it is configured to execute one or more of the methods described herein.

The controller may be integrated into the in-vitro diagnostic device, may be integrated into a functional unit or functional sub-unit of an in-vitro diagnostic device, or may be a separate logic entity in communication with the in-vitro diagnostic device or its functional units or functional sub-units via a direct connection, wired or wirelessly, or indirectly over a communications network, wired or wirelessly, such as a wide area network, e.g., the Internet or a Health Care Provider's local area network or intranet, via a network interface device. In some embodiments, the controller might be integral with a data management unit, e.g., implemented on a computing device such as a desktop computer, a laptop, a smartphone, a tablet, PDA, etc., may be comprised by a server computer and/or be distributed/shared across/between a plurality of in-vitro diagnostic devices. Moreover, the systems can include remote devices, servers and cloud-based elements that communicate via wires or wirelessly (e.g., infrared, cellular, Bluetooth®), or a remote PC/server or a cloud-based system. The processor may be also configurable to control the in-vitro diagnostic device in a way that workflow(s) and workflow step(s) are conducted by the in-vitro diagnostic device.

In particular, the controller is programmed to control the at least one pipetting unit to execute a number of scheduled process operations. The scheduled process operations may comprise any one or more of controlling the pipetting unit to penetrate the lid of a liquid container, measuring pressure, eventually re-penetrating the lid based on the pressure value detected within the liquid container, moving the pipetting unit to an aspiration position, to a dispensing position, to a start or end position, to a wash position, to a tip pick-up position, to a tip-waste position, and the like, aspirating a liquid from a liquid container, dispensing a liquid into a liquid container or into a waste reservoir, washing aspiration/dispensing probes and/or replacing disposable tips. The operation plan may however further comprise operations other than those associated with pipetting and moving of the pipetting unit. For example, the operation plan may comprise one or more scheduled process operations associated to functional units of the in-vitro diagnostic device other than the pipetting unit: moving of liquid containers, opening and/or closing of liquid containers, moving of reaction vessels, mixing of liquids, detecting the results of reactions, displaying the results to an operator. In particular, the controller may comprise a scheduler, for executing a sequence of steps within a predefined cycle time for a number of cycle times. The controller may further determine the order of in-vitro diagnostic tests according to the assay type, urgency, etc. The controller may further dynamically change the operation plan according to unusual occurring circumstances or newly occurring test orders or events.

According to an embodiment, the controller is configured to increase a pressure-event count number by one for each event that penetration is repeated and to control the pipetting unit to repeat penetration of the lid until a predetermined maximum number is reached. Once the pressure event count number reaches the predetermined maximum number, the controller controls the pipetting unit to abort lid penetration and prevents it from aspirating liquid from the liquid container. According to an embodiment, the controller may control the diagnostic device to move the liquid container to a liquid container output position. A device operator may then remove the liquid container from the in-vitro diagnostic device and manually remove the lid from the liquid container. The liquid container may then be re-inserted into the in-vitro diagnostic device. According to an embodiment, the controller may control the diagnostic device to move the liquid container to a liquid container decapping position for automatically removing the lid from the liquid container and optionally recapping the liquid container with the same or different lid, at the same position or at a different recapping position. According to an embodiment, even if the pressure event count number reaches the predetermined maximum number, the controller may control the pipetting unit to aspirate liquid from the liquid container, at the condition that the analytical result obtained therewith is flagged.

The "pressure-event count number" thereby represents the accumulated number of events that trigger the pipetting unit to repeat lid penetration for a specific liquid container. The measurement of a pressure outside of the predefined pressure range in said liquid container represents such a pressure event. The manufacturer of the in-vitro diagnostic device, or a field service representative (FSR), or an operator of the in-vitro diagnostic device may be able to determine a "maximum number" in the device settings that specifies the upper limit of allowable pressure events. For instance, the first time that the pipetting unit penetrates the lid of a specific liquid container and detects that the internal pressure falls outside of the predefined pressure range, a repetition of the lid penetration is automatically scheduled and the pressure-event count number for said liquid container is set from 0 to 1. When the pipetting unit then repeats lid penetration on the same liquid container, detects that the internal pressure is still outside of the predefined pressure range, a second repetition of the lip penetration is automatically scheduled and the pressure-event count number for that specific liquid container is set from 1 to 2, and so forth. Once the maximum number is reached, the controller controls the pipetting unit to abort the current lid penetration and prevents the pipetting unit from conducting any further lid penetrations or any aspiration or dispensing operations on the affected liquid container. Assuming that the maximum number is set to 3, the pipetting unit would repeat lid penetration on a specific liquid container three times in a row. Should the internal pressure at that stage still be outside of the predefined pressure range, the controller would detect that the maximum number has been reached and the process would be interrupted. The maximum number may be determined based for example on the type and/or brand of liquid container used in the laboratory, the lid material, the laboratory workflows, the number of processed samples in a given time period, the designated pipetting volume, the required pipetting precision, etc.

According to an embodiment, the controller is configured to control the pipetting unit to dispense gas into the liquid container upon detecting a pressure below the predefined pressure range before controlling the pipetting unit to repeat penetration. "Gas" can be any kind of gaseous substance that is introduced into the liquid container through the pipetting unit. The gas may be aspirated by the pipetting unit before penetrating the lid of the liquid container and be dispensed once the probe of the pipetting unit has penetrated the lid of the liquid container and a pressure below the predefined pressure range has been detected. The gas may therefore be air. The gas may also be introduced via the pipetting unit from a container holding the gas, e.g., in a compressed manner. Therefore, the fluid/gas channel of the pipetting unit would switch from a fluid aspirating/dispensing mode to a gas dispensing mode by, e.g., switching a corresponding valve so that the gas-holding container would be in connection with the probe of the pipetting unit. Examples of gaseous substances are nitrogen, noble gases or other inert gases or simply air. Either the volume of the introduced gas may be a fixed volume that has been determined in advance or it may correspond to a calculated volume that is required to compensate for the measured pressure difference, or sufficient to bring the pressure value within the pre-defined pressure range.

According to one embodiment, the controller is configured to control the pipetting unit to aspirate gas and/or a discardable volume of liquid from the liquid container upon detecting a pressure above the predefined pressure range before controlling the pipetting unit to repeat penetration. Either the volume of aspirated gas or aspirated liquid may be a predetermined and constant volume or it may correspond to a volume calculated to compensate for the measured pressure difference, or sufficient to bring the pressure value within the pre-defined pressure range. In contrast to an aliquot of liquid that is aspirated specifically for carrying out an in-vitro diagnostic test, the volume of liquid aspirated upon detecting overpressure is likely not precise and/or reliable and therefore is discarded in one of the following operation steps.

According to an embodiment, the controller is configured to control the pipetting unit to stop repeating penetration of the lid and/or to prevent dispensing gas or aspirating gas or liquid, if the pressure event count number reaches the predetermined maximum number.

According to an embodiment, the controller is configured to control the pipetting unit to penetrate the lid of the liquid container and to repeat penetration of the lid of the liquid container in different cycle times respectively. A "cycle time" as used herein, is a recurring time window, typically having a fixed length, during which a certain number of process operations are repeatedly carried out in a controlled sequence, called "cycle". Typically, in an in-vitro diagnostic device, many functional units and/or sub-units work in parallel. For example, a reaction vessel carrier may transport a reaction vessel from an initial position to a reaction position while a pipetting unit may aspirate liquid from a liquid container and at the same time an analytical measurement is performed. In certain situations, the functional units need to interact with each other, which requires timing their process operations to one another. E.g., handing over a reaction vessel from an incubation station to a measurement station requires timing the end of an incubation process with a free position on a reaction vessel carrier and a free position in the measurement station. In order to achieve an efficient synchronization of the process operations, a specific time period is defined in which several functional units may perform a specified sequence of process operations. This time period determines the duration of the cycle time. The controller is configured to schedule process operations for each functional unit according to the cadence of the cycle time and to synchronize the process operations in order to achieve maximal throughput for the in-vitro diagnostic device. For example, the process operations in one cycle time for a pipetting unit may comprise moving the pipetting unit from an initial position to a pipetting position, moving the probe of the pipetting unit into the liquid container placed in the pipetting position, performing an aspiration operation, moving the probe out of the liquid container, moving the pipetting unit to a liquid dispensing position, e.g., a reaction vessel or a waste position, performing a dispensing operation, moving the pipetting unit to a wash position, performing a wash procedure, and moving the pipetting unit back to the initial position. However, this does not necessarily mean that all process operations which are carried out in a cycle are repeated in another cycle. In particular, some process operations may repeatedly occur at every cycle, others may occur every two or more cycles.

Different diagnostic tests may require different process operations in a single cycle time. Since the controller needs to time multiple process operations for different functional units with each other, it is known for a person skilled in the art that a certain lead time is required on one hand to perform the scheduling calculations and on the other hand to transmit the instructions to each of the functional units. This typically happens some cycles before the process operations actually need to be performed by the functional units. Once the instructions have been transmitted, the sequence of process operations cannot be changed anymore. However, in case of an extraordinary event, e.g., in case of clogging of a pipetting device, in case of errors detected in pipetting or liquid level, in case of errors in handling vessels, or the like, respective measures have been implemented to interrupt or abort certain process operations in order to ultimately avoid incorrect measurement results and/or permanent damage of the functional units. In case of a pressure event in a closed liquid container, the controller, e.g., prevents the pipetting unit to aspirate an aliquot of the liquid for carrying out an in-vitro diagnostic test. Since the remaining operation steps in the same cycle time are already determined for the pipetting unit, the repetition of the lid penetration for the affected liquid container is scheduled by the controller for the next possible cycle time, in which the pipetting unit does not yet have any assigned process operations. Therefore, repetition of the lid penetration by the pipetting unit will be performed in a "different cycle time" than the initial lid penetration operation in order not to interfere with the remaining scheduled process operations and not to affect the interdependencies with other functional units and respective process operations already scheduled.

The present disclosure further refers to a computer implemented method for pipetting a liquid through a lid of a liquid container. The method comprises penetrating the lid of the liquid container by the pipetting unit and measuring the pressure in the liquid container by the pressure sensor. Upon detecting a pressure outside of a predefined pressure range in the liquid container, the method comprises repeating penetration of the lid of the liquid container, and only upon detecting a pressure within the predefined pressure range, aspirating an aliquot of the liquid for carrying out an in-vitro diagnostic test.

According to an embodiment, the method further comprises increasing a pressure-event count number by one for each event that penetration is repeated and controlling the pipetting unit to repeat penetration of the lid until a predetermined maximum number is reached.

According to an embodiment, the method further comprises dispensing a gas into the liquid container upon detecting a pressure below the predefined pressure range before repeating penetration.

According to an embodiment, the method further comprises aspirating gas and/or a discardable volume of liquid from the liquid container upon detecting a pressure above the predefined pressure range before repeating penetration.

According to an embodiment, the method further comprises stopping repeating penetration of the lid and/or preventing dispensing gas or aspirating gas or liquid, if the pressure event count number reaches the predetermined maximum number.

According to an embodiment, the method further comprises penetrating the lid of the liquid container and repeating penetration of the lid of the liquid container in different cycle times respectively.

Other and further objects, features and advantages will appear from the following description of exemplary embodiments and accompanying drawings, which serve to explain the principles more in detail.

FIG. 1 shows an example of an in-vitro diagnostic device 100. The in-vitro diagnostic device 100 comprises a sample loading/unloading unit 120 for loading/unloading sample tube racks 121 comprising sample tubes. The in-vitro diagnostic device 100 further comprises a central reaction vessel processing area 130. The reaction vessel processing area 130 comprises one linear static reaction vessel holder 150, the static reaction vessel holder 150 comprising a plurality of reaction vessel holding positions 151. The reaction vessel processing area 130 further comprises a movable reaction vessel carrier 160 linearly translational with respect to the static reaction vessel holder 140 and functionally coupled to the static reaction vessel holder 150 to transfer reaction vessels between reaction vessel holding positions 151 of the static reaction vessel holder 150. The in-vitro diagnostic device 100 comprises a reagent unit 140 for holding reagents to perform different diagnostic tests. The reagent unit 140 is embodied as a closed and tempered storage compartment, comprising access holes 141 for a pipetting probe to enter the compartment and withdraw an aliquot of reagent.

The system 100 further comprises a controller 170 programmed to control the execution of a number of scheduled process operations including operation of the pipetting unit 110 (described with reference to FIG. 2). In particular, the in-vitro diagnostic device 100 comprises a pipetting unit 110 comprising a pipetting probe (shown in FIG. 2). In particular, the pipetting unit 110 is mounted translationally on a horizontal arm 111 and the arm 111 is translationally coupled to an orthogonal guide rail 112. The pipetting unit 110 is thus movable in a space above the sample loading/unloading unit 120, above the reaction vessel processing area 130, and above the reagent unit 140. The pipetting probe is translationally movable in a vertical direction such as to be able to access a liquid container, as, e.g., a sample tube in the sample loading/unloading unit 120, a reaction vessel in the reaction vessel processing area 130, and/or a reagent container in the reagent unit 140 via holes 141. In particular, with the same pipetting unit 110, sample liquids can be aspirated from sample tubes in the sample loading/unloading unit 120, reagents can be aspirated from reagent containers in the reagent unit 140 and both sample liquids and reagents can be dispensed into reaction vessels in the reaction vessel processing area 130. The pipetting unit 110 may comprise different probes for pipetting samples and reagents respectively (not shown).

Figure 2:
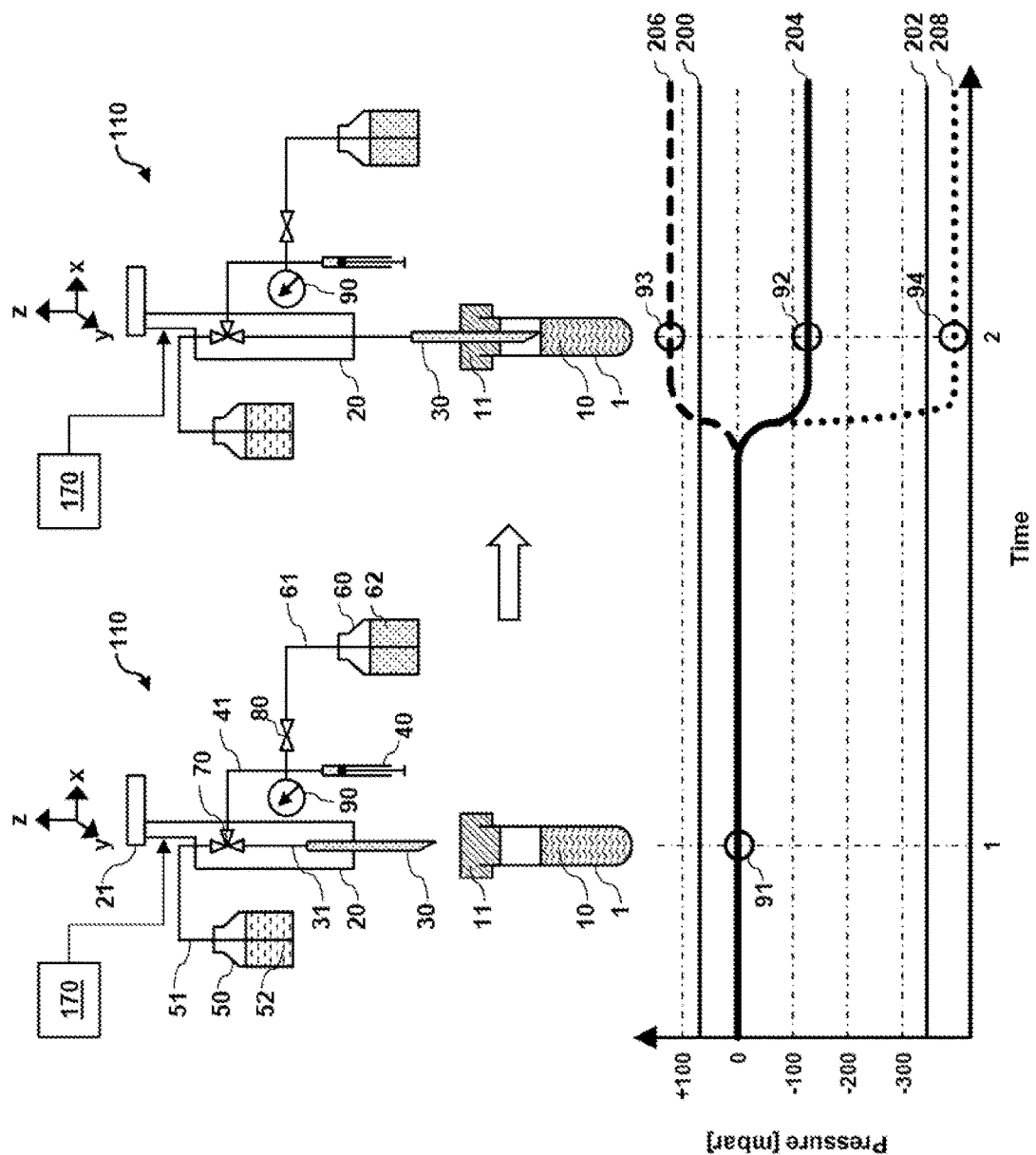
FIG. 2 shows schematically a pipetting unit and a method for pressure measurement in accordance with an embodiment of the instant disclosure.

FIG. 2 shows schematically an embodiment of the pipetting unit 110 of the in-vitro diagnostic device 100 of FIG. 1, configured for pipetting a liquid 10 from a liquid container 1. The pipetting unit 110 comprises a pipetting head 20 mounted on a x-y-z Cartesian head translation mechanism 21 that allows for movement in two directions of travel in a plane (x-y), e.g., with guiding rails, and in a third direction of travel orthogonal to the plane of translation (z-direction), e.g., with a spindle drive. The pipetting unit 110 further comprises a pipetting probe 30 attached to the pipetting head 20 for aspirating and dispensing liquids 10 from liquid containers 1. The probe 30 is connected to a pump 40, to a fluid supplier 50 comprising a wash solution 52, and to another fluid supplier 60 comprising system fluid 62 via multiple fluid/gas channels, i.e., a probe channel 31, a pump channel 41, a wash solution channel 51, and a system fluid channel 61, respectively. The pipetting unit 110 further comprises valves 70, 80 enabling fluid connections between certain channels while preventing fluid connections between other channels. A three-ports-two-positions valve 70 allows for a fluidic connection between the probe channel 31 and the pump channel 41, and the probe channel 31 and the wash solution channel 51, respectively. A two-ports-two-positions valve 80 allows for fluidic connection between the pump channel 41 and the system fluid channel 61. The controller 170 controls the valves 70, 80 depending on the planned or ongoing operation(s). For example, in a washing operation, the three-ports-two-positions valve 70 is operated such that the probe channel 31 has a fluidic connection to the wash solution channel 51, which then allows for rinsing the pipetting probe 30 with said wash solution 52 and at the same time preventing fluid flow from the pump channel 41. Analogously, the two-ports-two-positions valve 80 may be operated to prevent fluid flow from the system fluid channel 61 to the pump channel 41 when the probe channel 31 and the pump channel 41 have a fluidic connection, or to allow fluid flow from the system fluid channel 61 to the pump channel 41 when the probe channel 31 and the pump channel 41 are fluidically disconnected. In this example, the pump 40 is a syringe pump. The pipetting unit 110 uses the system fluid 62 in the syringe pump 40, the pump channel 41, the probe channel 31, and the pipetting probe 30 for hydraulic pumping by the pump 40. The pipetting unit 110 may be operated in a way that one or more air gaps are introduced in the pipetting probe 30 and/or the probe channel 31 to prevent the aspirated liquid 10 from a liquid container 1 from mixing with the system fluid 62 (not shown in figure). The pipetting unit 110 further comprises a pressure sensor 90 connected to the pump channel 41. The pressure sensor 90 allows to measure pressure changes at the tip of the pipetting probe 30 by conferring pressure changes via the fluid column or fluid/gas column being situated in the pipetting probe 30, the probe channel 31, and the pump channel 41 to the pressure sensor 90.

FIG. 2 also schematically illustrates a method for detecting pressure by the pipetting unit 110. Two consecutive steps are indicated by an arrow from left to right. A chart showing pressure measurements in mbar over time is placed below the schematic illustrations and corresponds to the respective steps. As illustrated in the first step, the pipetting unit 110 is in a state where the pipetting probe 30 is situated above a liquid container 1 closed by a lid 11 and containing liquid 10 after having received from the controller 170 an instruction to aspirate liquid 10 from said liquid container 1. In the embodiment illustrated in FIG. 2 the three-ports-two-positions valve 70 is adjusted so that a fluid connection between the probe channel 31 and the pump channel 41 is established. The pipetting probe 30, the probe channel 31, and the pump channel 41 are filled with system fluid 62. The liquid column formed thereby is used to measure the pressure at the tip of the pipetting probe 30 by the pressure sensor 90. Said pressure measurement 91 in the first step represents the "reference pressure", e.g., atmospheric pressure. However, in another embodiment not illustrated in FIG. 2, the reference pressure value may be a predefined value, eventually different from actual atmospheric pressure, which would implicate that a pressure measurement in the first step would not necessarily have to be conducted. The pipetting unit 110 is then instructed to move the pipetting head 20 in the z-direction and/or as illustrated the pipetting probe 30 in a translational movement with respect to the pipetting head 20 in the z-direction into the liquid container 1, thereby penetrating the lid 11 of the liquid container 1 with the pipetting probe 30. In a second step, when the tip of the pipetting probe 30 is inside the liquid container 10 above or at the surface of the liquid 1, the pressure is measured by the pressure sensor 90. This pressure measurement is referred to as "internal pressure", i.e., the pressure within the liquid container 1. FIG. 2 depicts three possible outcomes of the pressure measurement in the second step. In one example of pressure measurement 92, the measured pressure inside the liquid container 1 falls between a predefined upper threshold 200 and a predefined lower threshold 202, where the pressure measurement 92 lies on a continuous line 204 representing the pressure measured at the tip of the pipetting probe 30. The upper threshold 200 and the lower threshold 202 thereby confine the "predefined pressure range". It should be noted that the thresholds 200, 202 as illustrated in FIG. 2 are examples of possible thresholds determined by the device manufacturer, FSR, or device operator. However, they should not be construed as limited to this specific embodiment. The "predefined pressure range" may be defined by absolute numbers or by relative numbers with respect to the reference pressure. They may be based on, e.g., the designated pipetting volume and/or the required pipetting precision and may therefore differ from those illustrated in FIG. 2. The pressure measurement 92 is therefore considered lying "inside the predefined pressure range".

In another example of a pressure measurement 93, the measured pressure inside the liquid container 1 lies above the predefined upper threshold 200 at the measuring time point in the second step, where the dashed line 206 represents the pressure measured at the tip of the pipetting probe 30 when penetrating the lid 11 of a liquid container 1 with internal overpressure. Such a measurement is considered lying "outside of the predefined pressure range". In yet another example 94, the measured pressure inside the liquid container 1 lies below a predefined lower threshold 200 at the measuring time point in the second step, where the dotted line 208 represents the pressure measured at the tip of the pipetting probe 30 when penetrating the lid 11 of a liquid container 1 with internal negative pressure. Such a measurement is also considered lying "outside of the predefined pressure range".

Figure 3:
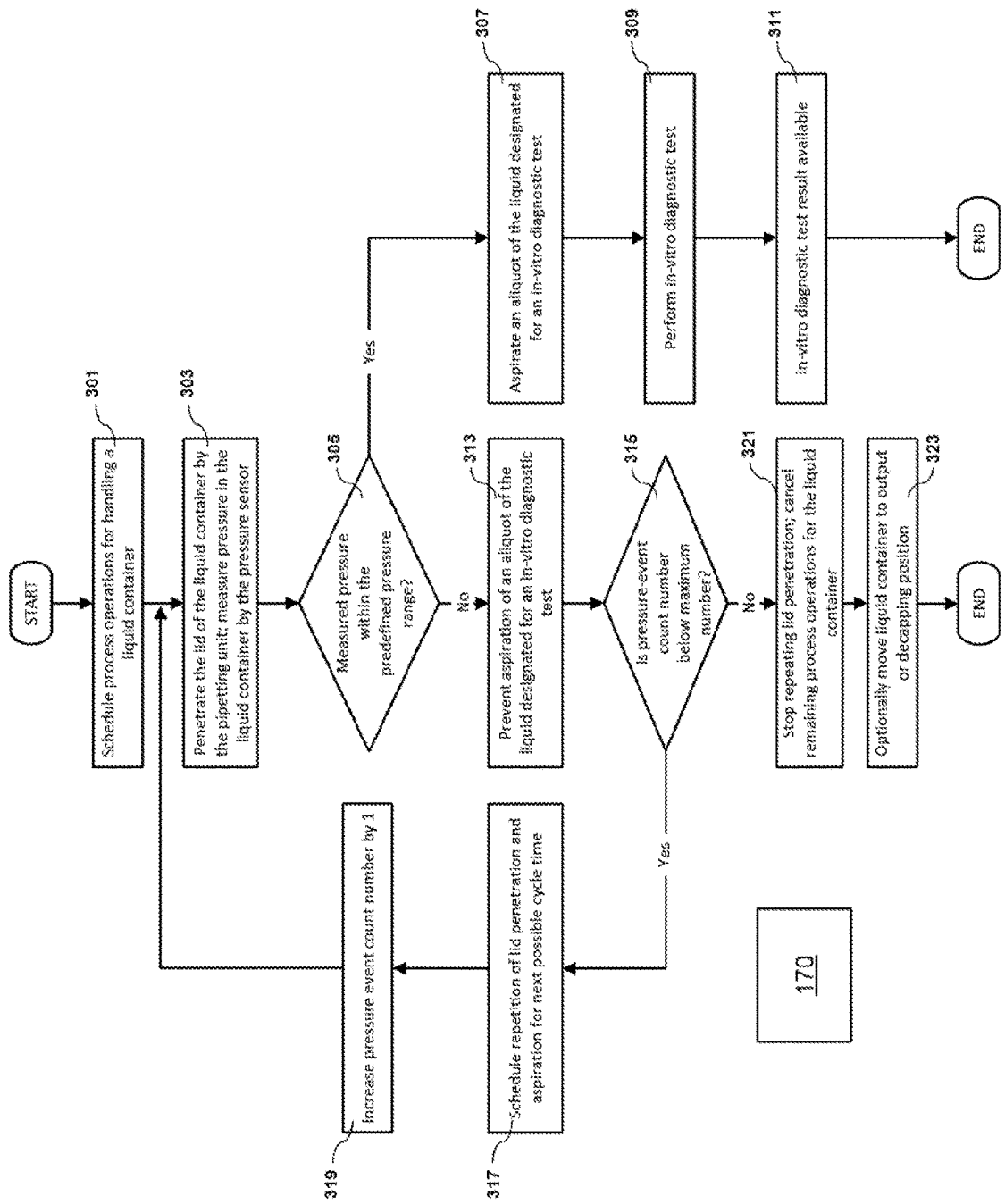
FIG. 3 shows a flow diagram of the method for pipetting a liquid through a lid of a liquid container.

FIG. 3 shows a flow diagram of a computer implemented method for pipetting a liquid through a lid of a liquid container according to the present disclosure. The method includes scheduling process operations for handling a given liquid container (step 301) according to, e.g., test orders that were received from a laboratory information system (LIS) or hospital information system (HIS) embedded in a Health Care Provider's local area network. In General, process operations are scheduled by the controller 170 for all functional units in an in-vitro diagnostic device required to perform process operations on said liquid container. In particular, process operations are scheduled for the pipetting unit of the in-vitro diagnostic device, synchronized with the process operations of all other functional units of the in-vitro diagnostic device, so that an efficient and time saving operation of the in-vitro diagnostic device can be ensured. Typically, process operations are scheduled to adhere to the cadence of a predefined cycle time. The pipetting unit is then controlled to execute process operations according to said schedule. For instance, following scheduled process operations for aspirating a liquid in a given closed liquid container, the pipetting unit penetrates the lid of said liquid container, where the pressure inside the liquid container is measured by the pressure sensor of the pipetting unit (step 303). The method further includes determining whether the pressure measured inside the liquid container falls into a predefined pressure range (step 305). If yes, the pipetting unit is controlled to continue the liquid aspiration operation by aspirating an aliquot of the liquid in the liquid container for carrying out an in-vitro diagnostic test (step 307). The aliquot is used for performing the in-vitro diagnostic test (step 309), which requires further process operations from the pipetting unit but also from functional units other than the pipetting unit. The in-vitro diagnostic test result may be reported to a device operator or physician when available (step 311). If the measured pressure in step 303 is determined to be outside of the predefined pressure range in step 305, i.e., above an upper threshold or below a lower threshold, the method includes preventing the pipetting unit from aspirating an aliquot of the liquid for carrying out an in-vitro diagnostic test (step 313). The method further comprises an automatic determination if the lid penetration can be repeated in order to at least partially compensate for overpressure or negative pressure in the liquid container. One variable contributing to the determination is based on checking whether the pressure-event count number is below a predetermined maximum number or whether it has reached the predetermined maximum number (step 315). If the pressure-event count number is below the predetermined maximum number, the method comprises triggering a repetition of the lid penetration and eventually liquid aspiration. Therefore, the controller 170 schedules the process operations of the pipetting unit related to a repetition of the lid penetration and liquid aspiration to the next available cycle time(s) (step 317), so the affected liquid container is processed with higher priority. Consequently, dependent process operations of other functional units related to handling the affected liquid container require rescheduling (not shown in FIG. 3). The method further comprises increasing the pressure-event count number by one for said liquid container (step 319). In the respective cycle time, the pipetting unit is then controlled to repeat penetration of the lid of said liquid container and measure the pressure inside said liquid container according to the rescheduled process operations (leading back to step 303 in the flow diagram). The method as shown in FIG. 3 corresponds to a feedback loop, achieving a (gradual) compensation or reduction of pressure difference between the inside and outside of a closed liquid container, while receiving feedback on the degree of compensation after each time lid penetration is repeated. However, if the pressure-event count number for a given liquid container reaches a predetermined maximum number in step 315, the method comprises aborting the current lid penetration, i.e., retracting the probe out of the liquid container and cancelling all remaining process operations scheduled for handling said liquid container 321, including specifically the process operations of the pipetting unit, e.g., aspirating or dispensing operations, but also further dependent process operations of other functional units. Particularly, the method includes stopping repeating lid penetration. In other words, the predetermined maximum number limits the number of attempts r for achieving sufficient pressure difference reduction or equilibration by repeated lid penetration. As illustrated in the example in FIG. 3, the liquid container may then be transported to a liquid container output position to, e.g., have the lid manually removed by a device operator or to an automatic decapping position (step 323).

Figure 4:
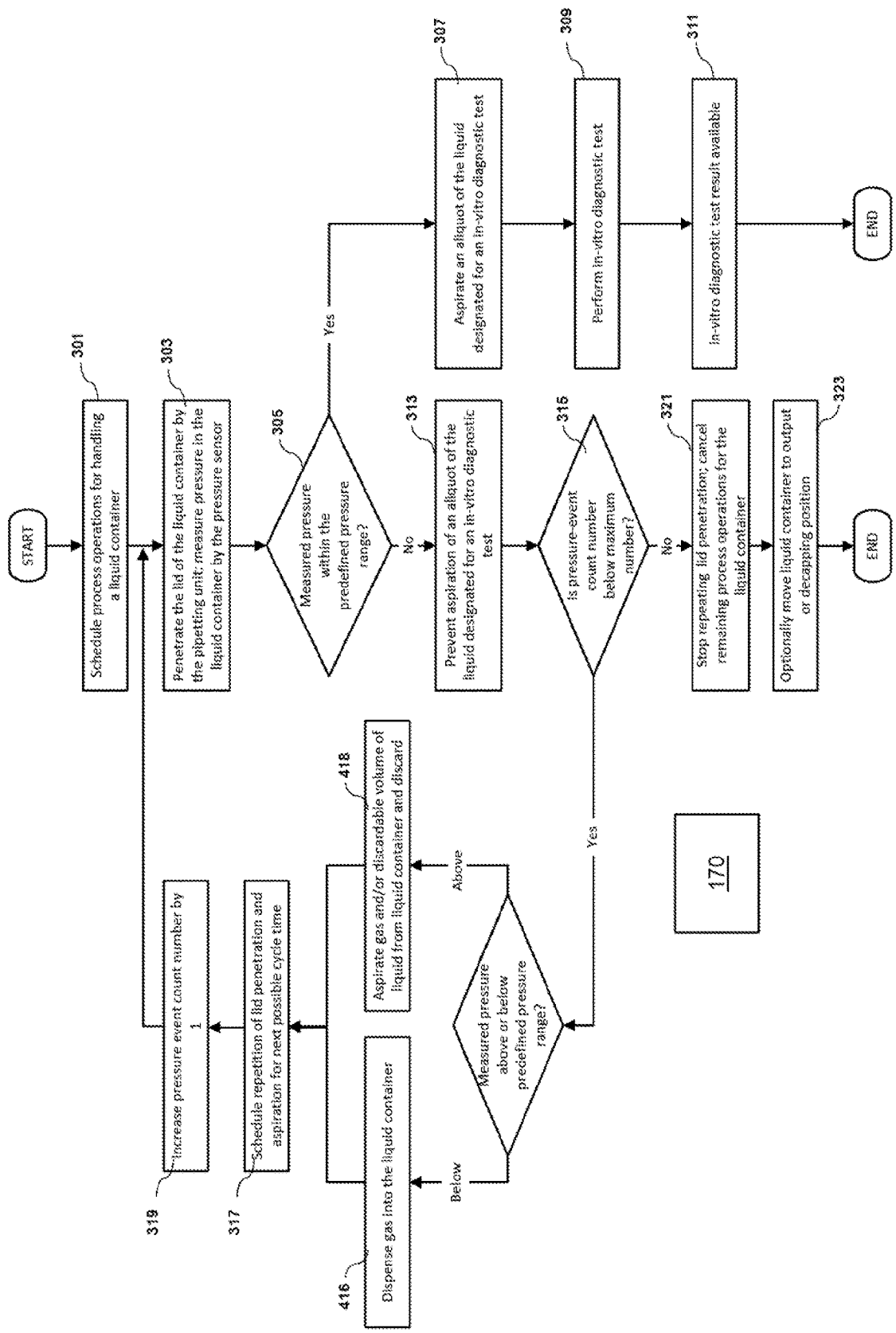
FIG. 4 shows a flow diagram of the method for pipetting a liquid through a lid of a liquid container according to further embodiments of the present disclosure.

FIG. 4 shows a flow diagram of a computer implemented method for pipetting a liquid through a lid of a liquid container according to further embodiments of the present disclosure. The method has many steps in common with the method illustrated in FIG. 3, with like steps being referred to by like reference numbers. These common steps will therefore not be addressed again. The difference to FIG. 3 however lies in certain automated steps that account for an actively supported pressure compensation. In particular, when starting from step 315, the method comprises determining whether the pressure-event count number is below a predetermined maximum number or whether it has reached the predetermined maximum number. In the event that the pressure-event count number is below the predetermined maximum number, the method further involves the pipetting unit to dispense a volume of gas into the liquid container (step 416), if the pressure measured inside the liquid container in step 303 was found to be below the predefined pressure range. Only after introducing gas into the liquid container for actively compensating the negative pressure, the controller will reschedule lid penetration for said liquid container for the next available cycle time (step 317) and increase the pressure-event count number by one (step 319). The method may require the pipetting unit to aspirate a volume of gas into the pipetting probe prior to penetrating the lid of the liquid container. The volume of gas may then be dispensed entirely or partially into the liquid container in step 416. On the other hand, in the event that the pressure being measured inside the liquid container in step 303 was found to be above the predefined pressure range, the method comprises controlling the pipetting unit to aspirate either a volume of gas and/or a discardable volume of liquid from the liquid container (step 418) for actively compensating the overpressure. In contrast to the aliquot of liquid aspirated for carrying out an in-vitro diagnostic test 407, the discardable volume of liquid aspirated for pressure equilibration 418 will be discarded in, e.g., a waste station. The discardable volume of liquid aspirated from the liquid container is not used for in-vitro diagnostic tests, because pipetting precision and reliability cannot be guaranteed in a liquid container with internal overpressure. The controller is configured to then schedule a repetition of the lid penetration for said liquid container for the next available cycle time (step 317) and increase the pressure-event count number by one (step 319). With reference to step 315, when the pressure-event count number reaches the predetermined maximum number, the method, analogously to the method illustrated in FIG. 3, comprises aborting the current lid penetration and cancelling all remaining process operations scheduled for handling the affected liquid container (step 321), including specifically the process operations of the pipetting unit, but also further dependent process operations of other functional units. In particular, this includes retracting the pipetting probe out of the liquid container and preventing the operations of dispensing gas (step 416) or aspirating gas and/or liquid (step 418) from the liquid container. Particularly, the method includes stopping repeating lid penetration.

It should be noted that FIG. 4 merely reflects one example of a computer implemented method. This example has implemented both variants of active pressure compensation, i.e., either by introducing air or by aspirating air/liquid from the liquid container depending on whether the liquid container contains a pressure above or below the predefined pressure range. In other examples only one of these active pressure compensation procedures may be implemented. Also the quantity of gas and/or liquid being dispensed/aspirated respectively may be calculated by the controller for achieve the desired amount of compensation whenever possible, e.g., based on the capacity of the probe, in one or consecutive penetration events, or be a predetermined quantity.

In the preceding specification, devices and methods according to various embodiments are described in detail. The devices and methods may be embodied in many different forms and should not be construed as limited to the embodiments set forth and illustrated herein. It is therefore to be understood that the devices and methods are not to be limited to the specific embodiments disclosed and that modifications and other embodiments are intended to be included within the scope of the appended claims. Although specific terms are employed herein, they are used in a generic and descriptive sense only and not for purposes of limitation. Unless defined otherwise, all technical and scientific terms used herein have the same meaning as commonly understood by one skilled in the art to which the disclosure pertains. Although any methods and materials similar to or equivalent to those described herein can be used in the practice or testing of the methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Also, reference throughout the specification to "one embodiment", "an embodiment", "one example" or "an example", means that a particular feature, structure or characteristic described in connection with the embodiment or example is included in at least one embodiment. Thus, appearances of the phrases "in one embodiment", "in an embodiment", "one example" or "an example", in various places throughout this specification are not necessarily all referring to the same embodiment or example. Furthermore, the particular features, structures, or characteristics may be combined in any suitable combinations and/or sub-combinations in one or more embodiments or examples.

Furthermore, the particular features, structures, or characteristics may be combined in any suitable combinations and/or sub-combinations in one or more embodiments or examples.

What is claimed is:

1. An in-vitro diagnostic device comprising:
   a pipetting unit for pipetting a liquid through a lid of a liquid container and comprising a pressure sensor for detecting a pressure in the liquid container; and
   a controller configured to control the pipetting unit to penetrate the lid of the liquid container, and
   upon the pressure sensor detecting the pressure in the liquid container outside of a predefined pressure range, the controller controlling the pipetting unit to repeat penetration of the lid in order to reduce pressure differences or achieve pressure equilibration between the interior of the liquid container and ambient conditions,
   wherein upon the pressure sensor detecting the pressure in the liquid container within the predefined pressure range, the controller controlling the pipetting unit to aspirate an aliquot of the liquid for carrying out an in-vitro diagnostic test.

2. The in-vitro diagnostic device according to claim 1, wherein the controller is configured to increase a pressure-event count number by one for each event that penetration is repeated and to control the pipetting unit to repeat penetration of the lid until a predetermined maximum number is reached.

3. The in-vitro diagnostic device according to claim 2, wherein the controller is configured to control the pipetting unit to stop repeating penetration of the lid and/or to prevent dispensing gas or aspirating gas or liquid, if the pressure event count number reaches the predetermined maximum number.

4. The in-vitro diagnostic device according to claim 1, wherein the controller is configured to control the pipetting unit to dispense gas into the liquid container upon detecting a pressure below the predefined pressure range before controlling the pipetting unit to repeat penetration.

5. The in-vitro diagnostic device according to claim 4, wherein the controller is configured to control the pipetting unit to dispense gas into the liquid container to increase the pressure in the liquid container.

6. The in-vitro diagnostic device according to claim 5, wherein the controller is configured to control the pipetting unit to dispense gas into the liquid container to increase the pressure in the liquid container to within the predetermined pressure range.

7. The in-vitro diagnostic device according to claim 1, wherein the controller is configured to control the pipetting unit to aspirate gas and/or a discardable volume of liquid from the liquid container upon detecting a pressure above the predefined pressure range before controlling the pipetting unit to repeat penetration.

8. The in-vitro diagnostic device according to claim 1, wherein the controller is configured to control the pipetting unit to penetrate the lid of the liquid container and to repeat penetration of the lid of the liquid container in different cycle times respectively.

9. A computer implemented method for pipetting a liquid through a lid of a liquid container, the method comprising:
   penetrating by a pipetting unit the lid of the liquid container;
   upon detecting a pressure in the liquid container outside of a predefined pressure range in the liquid container, repeating penetration of the lid with the pipetting unit to reduce pressure differences or achieve pressure equilibration between the interior of the liquid container and ambient conditions; and
   upon detecting a pressure in the liquid container within the predefined pressure range, aspirating an aliquot of the liquid for carrying out an in-vitro diagnostic test.

10. The method according to claim 9 further comprising increasing a pressure-event count number by one for each event that penetration is repeated and controlling the pipetting unit to repeat penetration of the lid until a predetermined maximum number is reached.

11. The method according to claim 9 further comprising dispensing a gas into the liquid container upon detecting a pressure below the predefined pressure range before repeating penetration.

12. The method according to claim 9 further comprising aspirating gas and/or a discardable volume of liquid from the liquid container upon detecting a pressure above the predefined pressure range before repeating penetration.

13. The method according to claim 9 further comprising stopping repeating penetration of the lid and/or preventing dispensing gas or aspirating gas or liquid, if the pressure event count number reaches the predetermined maximum number.

14. The method according to claim 9 further comprising penetrating the lid of the liquid container and to repeat penetration of the lid of the liquid container in different cycle times respectively.

* * * * *